United States Patent [19]

Willbanks

[11] Patent Number: 4,468,220

[45] Date of Patent: Aug. 28, 1984

[54] LOW FLOW CONSTANT RATE PUMP

[75] Inventor: Charles E. Willbanks, Spartanburg, S.C.

[73] Assignee: Milliken Research Corporation, Spartanburg, S.C.

[21] Appl. No.: 365,316

[22] Filed: Apr. 5, 1982

[51] Int. Cl.³ .............................................. A61M 1/00
[52] U.S. Cl. ................................... 604/133; 604/145; 604/890; 222/399
[58] Field of Search ............... 604/890, 891, 140, 145, 604/131, 133, 30; 222/386.5, 399

[56] References Cited

U.S. PATENT DOCUMENTS

| 2,962,196 | 11/1960 | Ayres | 222/399 |
| 3,023,750 | 3/1962 | Baron | 604/145 |
| 4,203,441 | 5/1980 | Theeuwes | 222/386.5 X |

Primary Examiner—Stephen C. Pellegrino
Attorney, Agent, or Firm—H. William Petry; Terry T. Moyer

[57] ABSTRACT

A low flow, constant rate pump is provided which comprises a fixed volume container, the inner walls of said container defining a receptacle for a liquid to be dispensed, said container being provided with means to form an unobstructed opening through which said liquid may be caused to flow continuously at a low-flow, constant rate, a propellant chamber within said container formed of a material which is permeable to vapor from a propellant of the liquid-vapor type, a supply of propellant of the liquid-vapor type confined within said chamber, said propellant initially being under pressure sufficient to maintain a major portion thereof in liquid form at normal temperatures.

1 Claim, 7 Drawing Figures

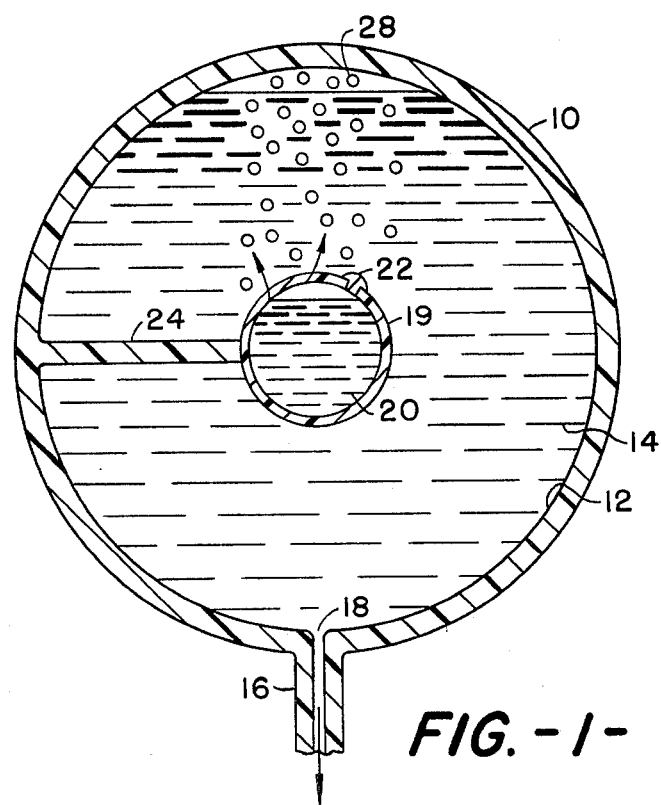
FIG.-1-
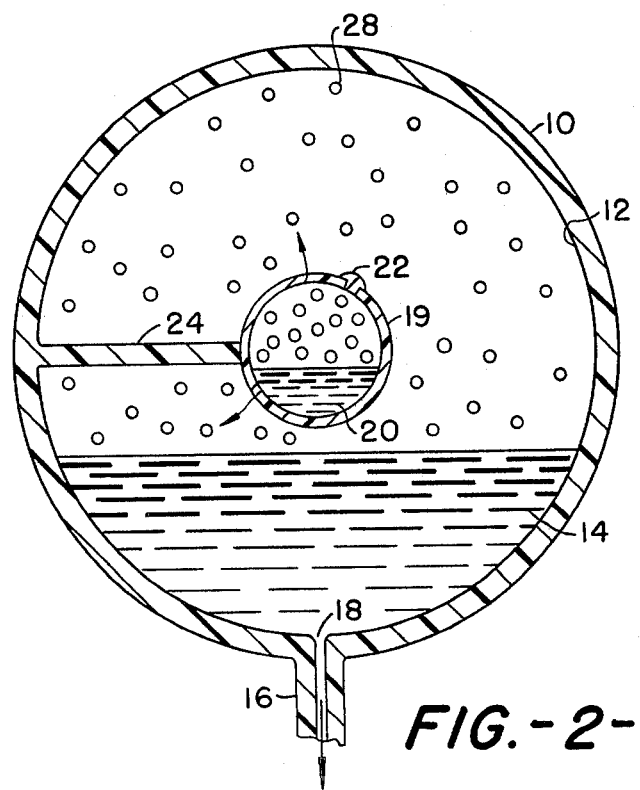
FIG.-2-

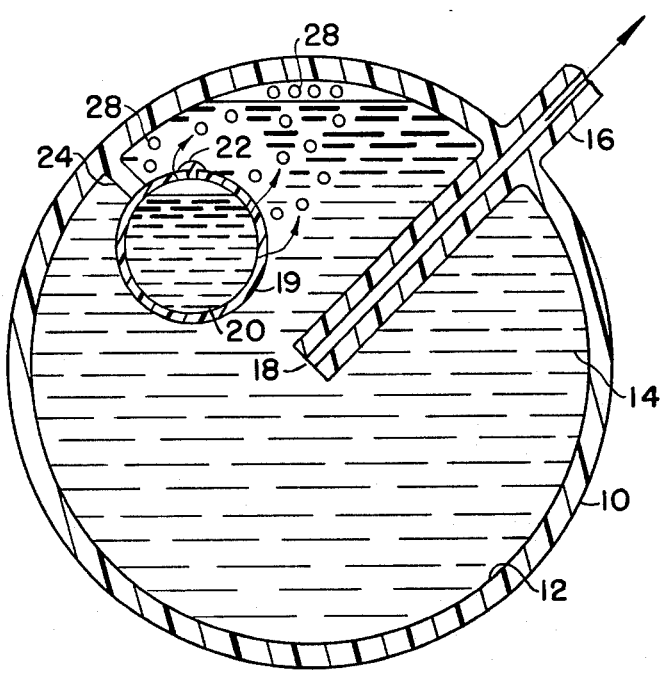
FIG.-3-
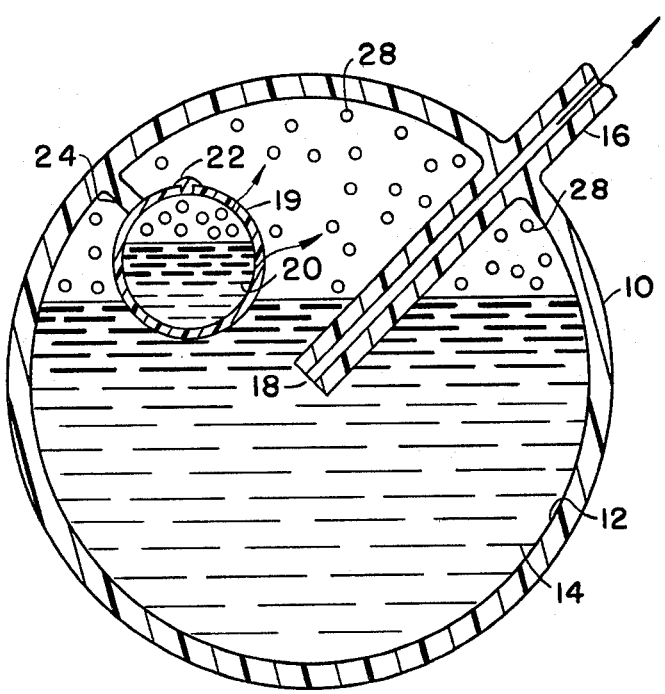
FIG.-4-

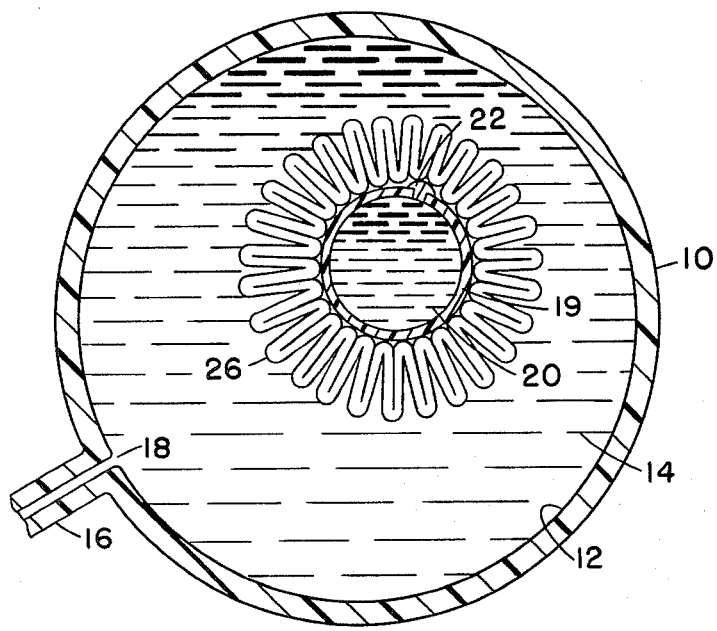
FIG.-5-
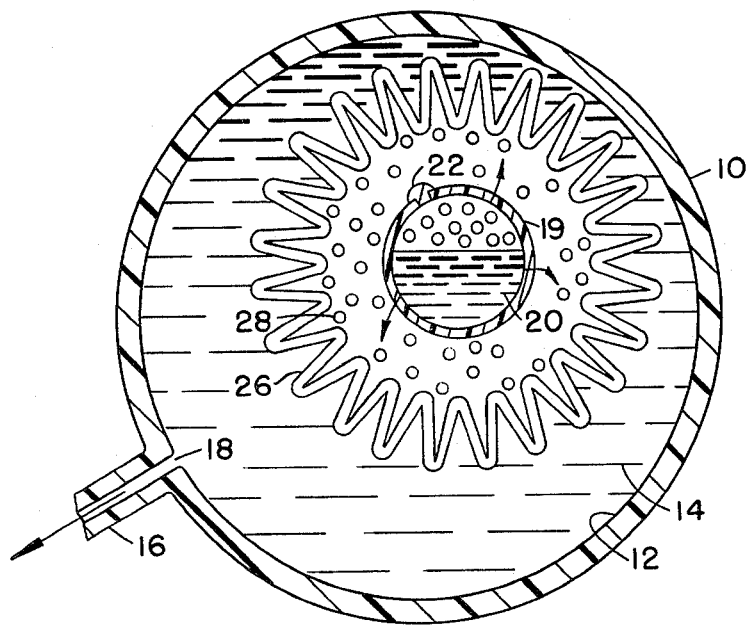
FIG.-6-

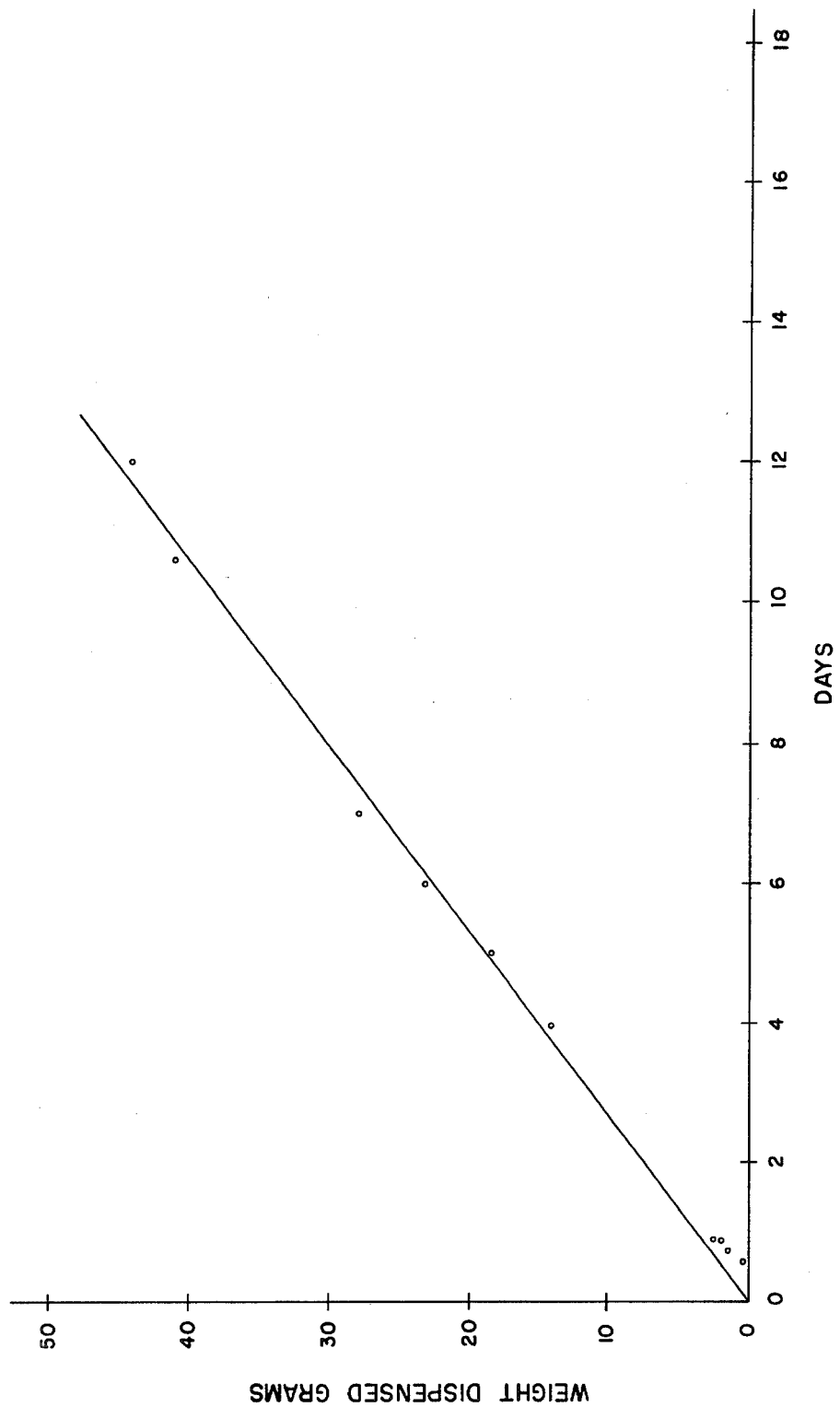
FIG.-7-

LOW FLOW CONSTANT RATE PUMP

The present invention relates to a low-flow, constant rate, multipurpose pump of simple design. More particularly, the present invention relates to a low flow, constant rate pump driven by the vapor created from a propellant of the liquid-vapor type.

Simple, inexpensive, low-flow, constant rate pumps requiring no extrinsic power source have long been sought. Such devices may have a wide range of end use applications where a constant, low volume supply of a liquid phase material is required. For instance, a readily apparent end use for such devices is in the administration of medications, e.g., drugs or other chemical substances, where typically such medications may be infused intravenously, intra-arterially, or into a body cavity or tissue at a constant volume, slow-flow, delivery rate. Thus, such devices may be used for such purposes as continuous heparinization, artificial pancreas, insulin injection, chemotherapeutic, organ infusion, anti-hyperlipidemic agent infusion, regional vasodilator infusion, and the like.

The present invention provides a low-flow, constant rate pump which is very versatile in its end use applications and which requires no external power source. The pump of the present invention may be particularly applicable for the administration of medications where the device may either by implanted subcutaneously or be worn by the patient externally while the medication is being administered.

Accordingly, the present invention relates to a low flow, constant rate pump which comprises a fixed volume container, the inner walls of said container defining a receptacle for a liquid to be dispensed, said container being provided with means to form an unobstructed opening through which said liquid may be caused to flow continuously at a low-flow, constant rate, a propellant chamber within said container formed of a material which is permeable to vapor from a propellant of the liquid-vapor type, a supply of propellant of the liquid-vapor type confined within said chamber, said propellant initially being under pressure sufficient to maintain a major portion thereof in liquid form at normal temperatures.

The present invention also relates to a method for the low flow, constant rate administration of a medication in liquid form to a patient, which comprises administering said medication by means of the pump mechanism described herein. The administration of the medication may be accomplished by implanting the pump subcutaneously or alternatively the pump may be conveniently worn by the patient during use with suitable conventional apparatus employed to transport the medicine from the pump container to the desired locality of administration, e.g., artery, body cavity, bodily organ and the like.

The container of the present invention may be constructed economically and conveniently from any of a wide variety of materials, e.g., metal, glass, plastic or any other suitable material. In general the material from which the container is constructed should be inert to the liquid to be dispensed and, in a preferred embodiment, the container may be constructed of a translucent or transparent material so that dispensing of the liquid may be monitored.

The container is provided with a means defining an opening in the container. The opening should be so constructed to allow the flow of fluid at a constant, predetermined rate. Thus, the opening should be large enough to allow for a substantially unobstructed flow of liquid, the rate of flow being determined by the rate at which the propellant vapor permeates through the chamber and displaces liquid to be dispensed within the container. Excessive pressures in substantial excess of atmospheric pressure are not allowed to develop within the container.

According to a preferred embodiment means defining said opening may be comprised of a conduit extending from the periphery of said container into the interstices of said container so that the portion of the opening in contact with the liquid is disposed at or near the concentric center of the pump. In this manner liquid will continue to be dispensed in any given orientation of the pump so long as the container is more than half filled with liquid. Such constructions for said pump may be particularly advantageous where the pump is disposed subcutaneously for the administration of liquid medications at a slow-flow, constant rate.

According to the invention the propellant is confined in a separate propellant chamber which may be constructed of any suitable propellant permeable material. Polyethylene has been found to be a suitable, inexpensive construction material. The propellant chamber may be filled with any of a wide range of liquid propellants, e.g., fluorochloromethanes, ethanes or mixtures thereof known commercially as "Freon" which are maintained at least initially in liquid form at normal temperatures by the pressure within the propellant chamber. Filling may be accomplished in any suitable manner and thereafter the opening through which the propellant is introduced into the propellant chamber is sealed by heat sealing or other suitable means. After the pump has been assembled for use and a full charge of liquid to be pumped has been provided the pump may be stored in an inactive state by simply closing off the opening in the container. The hydrostatic pressure created internally will prevent substantial quantities of propellant vapor from passing through the propellant chamber. When it is desired to commence pumping the opening is made and the initial pressure will quickly dissipate and a constant rate, low flow of liquid will commence.

According to an embodiment of the present invention the propellant chamber is encompassed by a flexible diaphragm. The diaphragm can be formed of any suitable material which will resist the chemical and solvent action of the liquid to be dispensed and of the propellant and which is impervious to both. The diaphragm may also, according to an embodiment, be expandable so that as the liquid is displaced from the container the volume of the propellant vapor may occupy the displaced liquid until the vapor occupies all or substantially all of the container volume when all of the liquid has been displaced. If the diaphragm is not expandable, it should nonetheless be flexible and be of such a size and shape so that when it is fully occupied by the propellant vapor all or substantially all of the liquid has been displaced from the container.

BRIEF DESCRIPTION OF THE DRAWINGS

For a fuller understanding of the nature of the invention, reference should be had to the following detailed description taken in connection with the accompanying drawings, in which:

FIGS. 1, 3 and 5 are views of medial sections of three different embodiments of the present invention upon commencement of the pumping operation.

FIGS. 2, 4 and 6 are views of medial sections of the same embodiments shown in FIGS. 1, 3 and 5 respectively showing the pump and liquid configuration after some quantity of liquid has been dispensed from the pump.

DETAILED DESCRIPTION OF THE DRAWINGS

In the drawings identical numbers used in different figures refers to corresponding parts of the apparatus. Turning now to FIGS. 1 and 2 which depict an embodiment of the pump mechanism of the present invention, fixed volume container 10 is provided with inner walls 12 which define a receptacle for liquid 14. Container 10 is provided with means 16 defining an opening 18 in the container through which liquid 14 may pass at a low flow, constant rate. Also provided within container 10 is a propellant chamber 19 containing propellant 20 made of a propellant-vapor permeable material such as polyethylene. The propellant chamber is provided with a plug 22 to seal off the chamber after charging with propellant and the chamber is attached in a fixed position within the container by rod 24.

FIG. 1 illustrates the invention at or soon after the commencement of the dispensing operation. At this time the propellant chamber 19 may be filled with a substantial quantity of propellant liquid. This liquid 14 to be dispensed also occupies all or substantially the entire volume of the receptacle formed by the inner walls 12 of container 10. Then, as liquid is dispensed and as propellant migrates through propellant chamber 19, liquid phase propellant is observed to co-exist in equilibrium with vapor phase propellant. In addition as FIG. 2 illustrates, vapor phase propellant occupies the space vacated by the liquid 14 in the receptacle.

FIGS. 3 and 4 illustrate another embodiment of the present invention where means 16 defining the opening in container 10 is the form of a conduit so that the opening 18 is disposed at or near the concentric center of the pump. The propellant chamber is attached in a fixed position by rod 24 at a position removed from the concentric center of the pump. FIG. 3 illustrates the pump in a filled position at commencement of pumping of the liquid so that propellant liquid 20 occupies a substantial volume of propellant chamber 19. The liquid to be dispensed also occupies a substantial volume of the receptacle defined by inner walls 12. As shown in FIG. 2 after some portion of liquid 14 has been dispensed gasseous propellant occupies the space vacated by the liquid and liquid propellant exists in equilibrium with vapor phase propellant in propellant chamber 19.

FIGS. 5 and 6 illustrate yet another embodiment of the present invention where the propellant chamber 19 is encompassed by flexible diaphragm 26 which serves to separate vapor phase propellant 28 which has migrated out of the propellant chamber from the liquid 14 to be dispensed. FIG. 5 illustrates the pump at the commencement of operation showing the diaphragm in a substantially collapsed position and a high level of propellant liquid 20 in propellant chamber 19. As vapor phase propellant migrates through the walls of the propellant chamber the space vacated by liquid as it is dispensed is simultaneously occupied by vaporous propellant 28 separated from liquid 14 by diaphragm 26. As can be observed in this embodiment opening 18 may be provided at virtually any location without resulting in a disturbance of liquid flow as it is being dispensed.

EXAMPLE

A polyethylene vial (disposable pipette) was filled with 2 cc of liquid Freon and the end was heat sealed. The sealed tube was placed in a one liter glass bottle which was filled with water. A one-hole stopper was inserted into the opening of the bottle and through the opening in the stopper was inserted a capillary tube having an interior diameter of 0.05 cm. The bottle was placed on its side and the amount of water pumped was measured over a fourteen day period. The data is summarized in FIG. 7 and shows a slow flow, very constant rate of dispensing liquid from the pump.

It will be understood that various modifications may be made in practicing the invention and in the embodiments of the invention shown and described herein without departing from the scope of the invention as defined by the following claims.

What is claimed is:

1. A low flow, constant rate pump which comprises a fixed volume container, the inner walls of said container defining a receptacle for a liquid to be dispensed, said container being provided with means to form an unobstructed opening through which said liquid may be caused to flow continuously at a low-flow, constant rate, a propellant chamber within said container formed of a material which is permeable to vapor from a propellant of the liquid-vapor type, a supply of propellant of the liquid-vapor type confined within said chamber, said propellant initially being under pressure sufficient to maintain a major portion thereof in liquid form at normal temperatures, and wherein said propellant chamber within said container is itself encompassed by a flexible diaphragm impermeable to said propellant vapor and to said liquid to be dispensed, thereby separating said propellant vapor from said liquid.

* * * * *